United States Patent
Tsai et al.

(10) Patent No.: US 11,246,204 B2
(45) Date of Patent: Feb. 8, 2022

(54) METHOD FOR CONTROLLING ULTRAVIOLET LAMP AND ELECTRONIC DEVICE

(71) Applicant: TRIPLE WIN TECHNOLOGY(SHENZHEN) CO. LTD., Shenzhen (CN)

(72) Inventors: Wen-Chin Tsai, Shenzhen (CN); Cong Zhu, Shenzhen (CN)

(73) Assignee: TRIPLE WIN TECHNOLOGY(SHENZHEN) CO. LTD., Shenzhen (CN)

(*) Notice: Subject to any disclaimer, the term of this patent is extended or adjusted under 35 U.S.C. 154(b) by 31 days.

(21) Appl. No.: 16/988,899

(22) Filed: Aug. 10, 2020

(65) Prior Publication Data
US 2021/0400785 A1    Dec. 23, 2021

(30) Foreign Application Priority Data
Jun. 17, 2020  (CN) .......................... 202010551616.3

(51) Int. Cl.
*H05B 47/11* (2020.01)
*A61L 2/10* (2006.01)

(52) U.S. Cl.
CPC ................ *H05B 47/11* (2020.01); *A61L 2/10* (2013.01)

(58) Field of Classification Search
CPC ...... H05B 47/11; H05B 47/105; H05B 47/10; A61L 2/10; F21V 14/00; F21V 14/02; F21V 21/14; F21V 99/00; H01J 2237/20; H01J 2237/202; H01J 2237/20278; H01J 2237/20285; G01N 21/00; G01N 2021/0125; G01N 2021/0162; G01N 21/01
See application file for complete search history.

(56) References Cited

U.S. PATENT DOCUMENTS

| | | | | |
|---|---|---|---|---|
| 6,801,650 B1* | 10/2004 | Kikuchi | ............. | G01R 31/2887 382/145 |
| 6,807,906 B1* | 10/2004 | DeMoore | ............ | B41F 23/0443 101/424.1 |
| 2015/0146181 A1* | 5/2015 | Chen | ................. | G02F 1/133711 355/67 |
| 2019/0299260 A1* | 10/2019 | Shatalov | ................... | A61L 2/10 |

FOREIGN PATENT DOCUMENTS

TW    I456564    10/2014

* cited by examiner

*Primary Examiner* — Bao Q Truong
(74) *Attorney, Agent, or Firm* — ScienBiziP, P.C.

(57) ABSTRACT

A method for controlling an ultraviolet lamp for even and uniform irradiation of curable glue on a product includes obtaining tilt data of a platform of a machine, where the tilt data comprises a tilt direction and a tilt angle, and calculating a tilt amplitude of the platform of the machine based on the tilt data. The method further includes determining an ultraviolet lamp as a target to be adjusted based on the tilt direction, and obtaining an adjustment range of the target ultraviolet lamp based on the calculated tilt amplitude, and sending the adjustment range to an ultraviolet lamp adjustment device to adjust the target ultraviolet lamp. So that ultraviolet light emitted by the target ultraviolet lamp can illuminate the product to be irradiated on the platform in parallel.

15 Claims, 4 Drawing Sheets

METHOD FOR CONTROLLING ULTRAVIOLET LAMP AND ELECTRONIC DEVICE

CROSS-REFERENCE TO RELATED APPLICATIONS

This application claims priority to Chinese Patent Application No. 202010551616.3 filed on Jun. 17, 2020, the contents of which are incorporated by reference herein.

FIELD

The subject matter herein generally relates to ultraviolet lamp controlling technology.

BACKGROUND

In a production process, it is often necessary to use ultraviolet lamps to cure glue by irradiation to achieve product assembly and bonding. At present, an operator may be able to use hexagonal screws to adjust the position of the ultraviolet lamp. In the production process, if the position of the ultraviolet lamp is shifted, the surface being irradiated will effectively be rendered uneven, so that the assembled product will not meet requirements.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
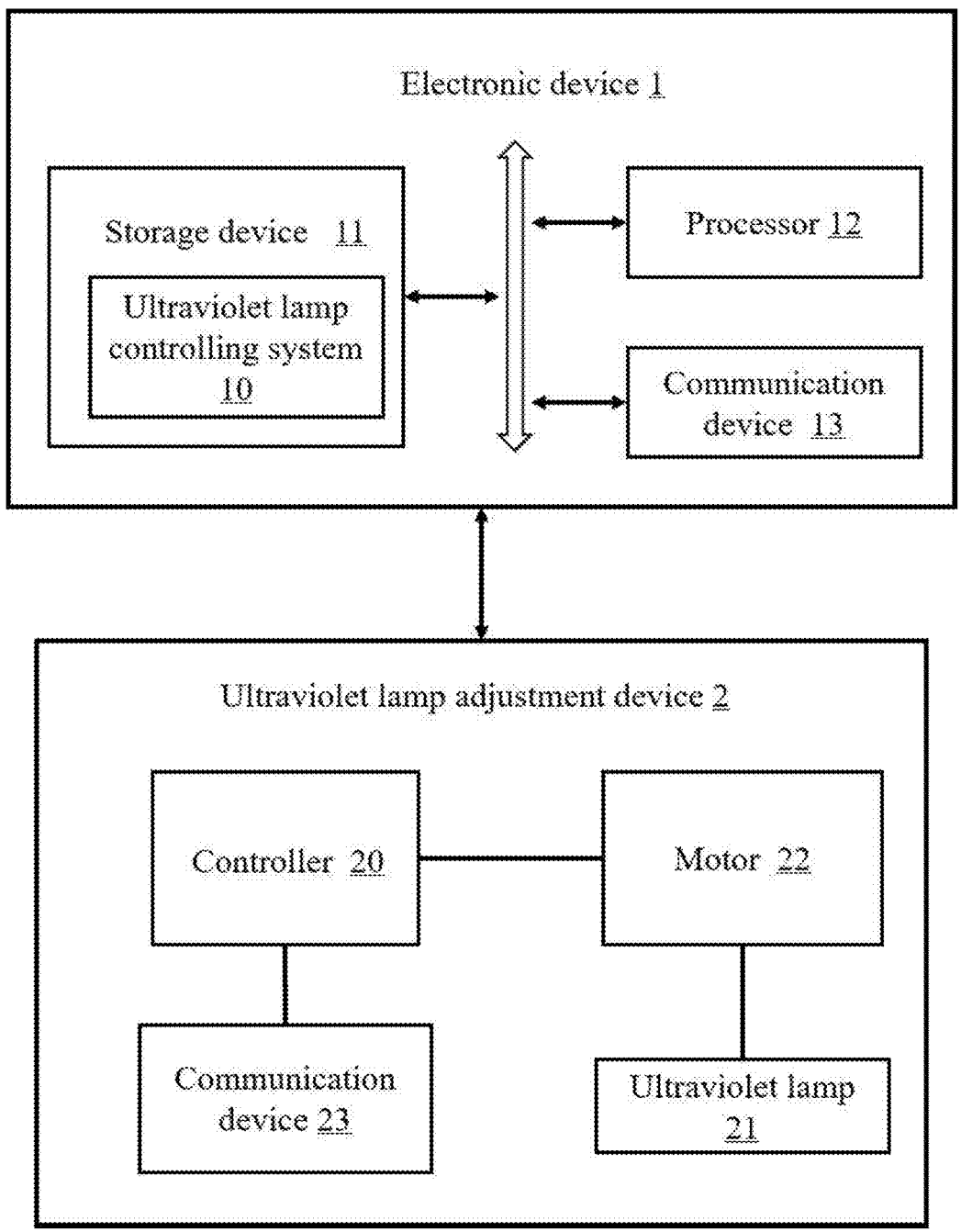
FIG. 1 illustrates an application environment architecture diagram of a method for controlling an ultraviolet lamp.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The present disclosure, including the accompanying drawings, is illustrated by way of examples and not by way of limitation. It should be noted that references to "an" or "one" embodiment in this disclosure are not necessarily to the same embodiment, and such references mean "at least one."

The term "module", as used herein, refers to logic embodied in hardware or firmware, or to a collection of software instructions, written in a programming language, such as, Java, C, or assembly. One or more software instructions in the modules can be embedded in firmware, such as in an EPROM. The modules described herein can be implemented as either software and/or hardware modules and can be stored in any type of non-transitory computer-readable medium or other storage device. Some non-limiting examples of non-transitory computer-readable media include CDs, DVDs, BLU-RAY™, flash memory, and hard disk drives. The term "comprises" means "including, but not necessarily limited to"; it specifically indicates open-ended inclusion or membership in a so-described combination, group, series, and the like.

FIG. 1 is an application environment diagram of one embodiment of a method for controlling an ultraviolet lamp 21. The method is applied in an electronic device 1, and the electronic device 1 communicates with an ultraviolet lamp adjustment device 2 for adjusting the working of the ultraviolet lamp 21. Depending on the embodiment, the electronic device 1 can include, but is not limited to, a storage device 11, at least one processor 12, and a communication device 13. The storage device 11, the at least one processor 12, and the communication device 13 communicate with each other directly or through a system bus.

In at least one embodiment, the storage device 11 may be an internal memory of the electronic device 1. That is, the storage device 11 may be built in the electronic device 1. In other embodiments, the storage device 11 may also be an external memory of the electronic device 1. That is, the storage device 11 can be externally connected to the electronic device 1.

In at least one embodiment, the storage device 11 may be used to store computer programs and various data of computer programs. For example, the storage device 11 may be used to store an ultraviolet lamp controlling system 10 installed in the electronic device 1.

Figure 3:
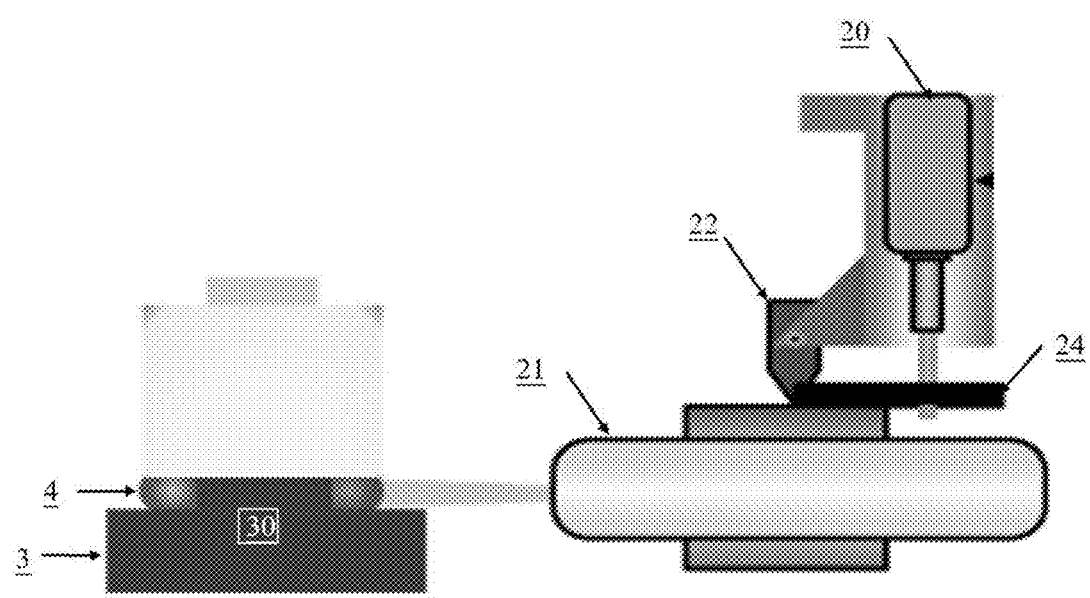
FIG. 3 is a schematic diagram of the ultraviolet lamp irradiating a product with UV light.

In at least one embodiment, the storage device 11 can store data of a platform of a machine (e.g., a machine 3 in FIG. 3). The platform is used to hold a product to be irradiated. The data is acquired when the product is placed on the platform. In general, the platform will tilt if the product is placed on it. If an irradiation direction of the ultraviolet lamp 21 is not adjusted, an irradiated surface of the product is effectively uneven, which may cause the product not to meet a specification.

For example, if the products are lens and chip, the lens is needed to be glued with the chip. The chip can be placed on the platform, the lens is fixed on the chip with glue, and then the ultraviolet lamp 21 of the ultraviolet lamp adjustment device 2 emits ultraviolet light on the glue, to cure the glue evenly between the lens and the chip. In general, the platform will tilt when the chip is placed thereon. If an irradiation direction of the ultraviolet lamp 21 is not adjusted. Then, an irradiated surface of the glue is uneven.

In at least one embodiment, the storage device 11 may include Read-Only Memory (ROM), Programmable Read-Only Memory (PROM), Erasable Programmable Read-Only Memory (EPROM), One-time Programmable Read-Only Memory (OTPROM), Electronically Erasable Programmable Read-Only Memory (EEPROM), Compact Disc Read-Only Memory (CD-ROM) or other optical disk storage, magnetic disk storage, magnetic tape storage, or any other non-volatile computer-readable storage medium that can be used to carry or store data.

In at least one embodiment, the processor 12 may be a central processing unit (Central Processing Unit, CPU), or other general-purpose processors, digital signal processors (DSP), application specific integrated circuits (ASIC), Ready-made programmable gate array (Field-Programmable Gate Array, FPGA) or other programmable logic devices, discrete gate or transistor logic devices, discrete hardware components, etc. The general-purpose processor may be a microprocessor or the processor 12 may also be any other conventional processor.

In at least one embodiment, the ultraviolet lamp adjustment device 2 can include a controller 20, the ultraviolet lamp 21, a motor 22, and a communication device 23. The controller 20 is electrically connected to the ultraviolet lamp 21, the motor 22, and the communication device 23.

In at least one embodiment, the controller 20 may be a programmable logic controller (PLC). The controller 20 can control the motor 22 to adjust direction and amplitude of the ultraviolet lamp 21, through a connecting device 24 (shown in FIG. 3). The connecting device 24 is connected with the ultraviolet lamp 21.

In at least one embodiment, the communication devices 13 and 23 can provide a network communication function for the electronic device 1 and the ultraviolet lamp adjustment device 2 through a wired or wireless network transmission method. The wired network can be any type of wired communication, such as the Internet and a local area network. The wireless network can be any type of wireless communication, such as BLUETOOTH, radio, WI-FI, cellular, satellite, broadcasting, etc.

FIG. 1 illustrates only one example of the electronic device 1, other examples can comprise more or fewer components that those shown in the embodiment, or can have a different configuration of the various components. The electronic device 1 may be a mobile phone, a tablet computer, a digital assistant, a personal computer, or any other suitable device.

Figure 2:
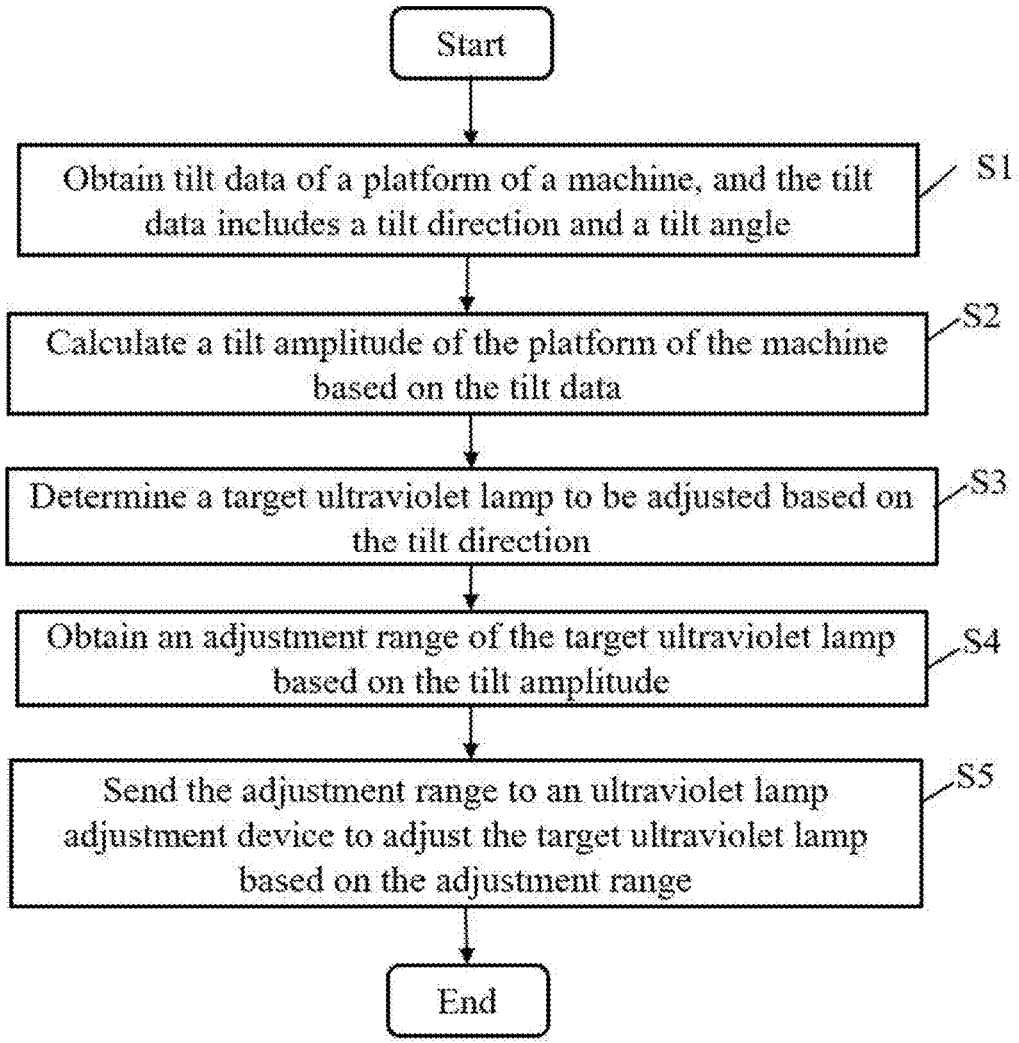
FIG. 2 illustrates a flowchart of one embodiment of the method for controlling the ultraviolet lamp.

FIG. 2 illustrates a flowchart of the method for controlling the ultraviolet lamp 21. Referring to FIG. 2, the method is provided by way of example, as there are a variety of ways to carry out the method. The method described below can be carried out using the configurations illustrated in FIG. 1, for example, and various elements of these figures are referenced in explaining method. Each block shown in FIG. 2 represents one or more processes, methods, or subroutines, carried out in the method. Furthermore, the illustrated order of blocks is illustrative only and the order of the blocks can be changed. Additional blocks can be added or fewer blocks can be utilized without departing from this disclosure. The example method can begin at block S1.

At block S1, the electronic device 1 can obtain tilt data of a platform of the machine 3, and the tilt data includes a tilt direction and a tilt angle.

In at least one embodiment, in an initial state, the platform of the machine 3 and the ultraviolet lamp 21 are at the same level, and a product to be irradiated is placed on the platform of the machine 3.

It should be noted that during a manufacturing process of the product, the electronic device 1 can obtain the tilt data of the platform of the machine 3 in real time.

In at least one embodiment, the machine 3 can include a tilt sensor 30 which is placed on the platform, and the tilt sensor can detect the tilt data of the platform of the machine 3. The tilt sensor can communicate with the electronic device 1. It should be noted that the tilt sensor may be a dual-axis tilt sensor, which can detect the tilt angle and the tilt direction of the platform of the machine 3, and send the tilt angle and the tilt direction to the electronic device 1.

At block S2, the electronic device 1 can calculate a tilt amplitude of the platform of the machine 3 based on the tilt data.

In at least one embodiment, the electronic device 1 can calculate the tilt amplitude of the platform of the machine 3 based on the tilt angle and the tilt direction. The electronic device 1 can establish a coordinate system based on the platform being in an initial horizontal state, where an origin of the coordinate system is a point of a lower left corner of the platform. An X-axis of the coordinate system is a length of the platform, and a Y-axis of the coordinate system is a width of the platform. The electronic device 1 can calculate a first tilt amplitude of the platform of the machine 3 in the X-axis direction based on the length of the machine 3 in the X-axis direction and the tilt angle, and calculate a second tilt amplitude of the platform of the machine 3 in the Y-axis direction based on the width of the machine 3 in the Y-axis direction and the tilt angle.

In at least one embodiment, the tilt amplitude of the platform of the machine 3 can include a first tilt width of the platform of the machine 3 in the X-axis direction and a second tilt width of the platform of the machine 3 in the Y-axis direction of the coordinate system. When the platform of the machine 3 is tilted below the horizontal plane, the tilt amplitude is negative, and when the platform of the machine 3 is tilted above the horizontal plane, the tilt amplitude is positive.

At block S3, the electronic device 1 can determine a target ultraviolet lamp to be adjusted based on the tilt direction.

In at least one embodiment, the electronic device 1 can determine a tilted portion of the platform of the machine 3 based on the tilt direction, and determine the target ultraviolet lamp based on the tilted portion of the platform of the machine 3. In at least one embodiment, the electronic device 1 can pre-store a correspondence table between the tilted portion of the platform of the machine 3 and the ultraviolet lamp 21. Then, the electronic device 1 can determine the target ultraviolet lamp based on the tilted portion of the platform of the machine 3 by querying the correspondence table.

For example, the platform of the machine 3 is rectangular in shape. A total number of the ultraviolet lamps 21 is at least four. The four ultraviolet lamps 21 are set in line with four corners of the platform of the machine 3, so that the product can be evenly irradiated. For example, the four ultraviolet lamps 21 can include a first ultraviolet lamp, a second ultraviolet lamp, a third ultraviolet lamp, and a fourth ultraviolet lamp. The first ultraviolet lamp corresponds to an upper left corner of the platform of the machine 3, the second ultraviolet lamp corresponds to a lower left corner of the platform of the machine 3, the third ultraviolet lamp corresponds to an upper right corner of the platform of the machine 3, and the fourth ultraviolet lamp corresponds to a lower right corner of the platform of the machine 3.

In at least one embodiment, when the platform of the machine 3 is tilted, the electronic device 1 can determine the target ultraviolet lamp according to the tilt direction of the machine 3. For example, when the platform of the machine 3 is tilted to the lower left corner, the electronic device 1 can determine that the tilted portion of the platform of the machine 3 is the lower left corner through the tilt sensor, and determine that the second ultraviolet lamp is the target ultraviolet lamp. When the platform of the machine 3 is tilted to the upper left corner, the electronic device 1 can determine that the tilted portion of the platform of the machine 3 is the upper left corner through the tilt sensor, and determine that the first ultraviolet lamp is the target ultraviolet lamp. When the platform of the machine 3 is tilted to the lower right corner, the electronic device 1 can determine that the tilted portion of the platform of the machine 3 is the lower right corner through the tilt sensor, and determine that the fourth ultraviolet lamp is the target ultraviolet lamp. When the platform of the machine 3 is tilted to the upper right corner, the electronic device 1 can determine that the tilted portion of the platform of the machine 3 is the upper right corner through the tilt sensor, and determine that the third ultraviolet lamp is the target ultraviolet lamp.

At block S4, the electronic device 1 can obtain an adjustment range of the target ultraviolet lamp based on the tilt amplitude.

In at least one embodiment, the electronic device 1 can obtain the adjustment range based on the tilt amplitude after determining the target ultraviolet lamp, and make the ultraviolet light emitted by the target ultraviolet lamp and the product to be irradiated are at the same level.

At block S5, the electronic device 1 can send the adjustment range to the ultraviolet lamp adjustment device 2 to adjust the target ultraviolet lamp based on the adjustment range.

In at least one embodiment, the electronic device 1 can send the adjustment range to the ultraviolet lamp adjustment device 2. The controller 20 of the ultraviolet lamp adjustment device 2 controls the motor 22 to rotate the connecting device 24 connected to the target ultraviolet lamp to move the target ultraviolet lamp upward or downward, so that the ultraviolet light emitted by the target ultraviolet lamp can illuminate the product to be irradiated on the platform in parallel. That is, the ultraviolet light emitted by the target ultraviolet lamp and the product to be irradiated are on the same horizontal plane, as shown in FIG. 3.

Figure 4:
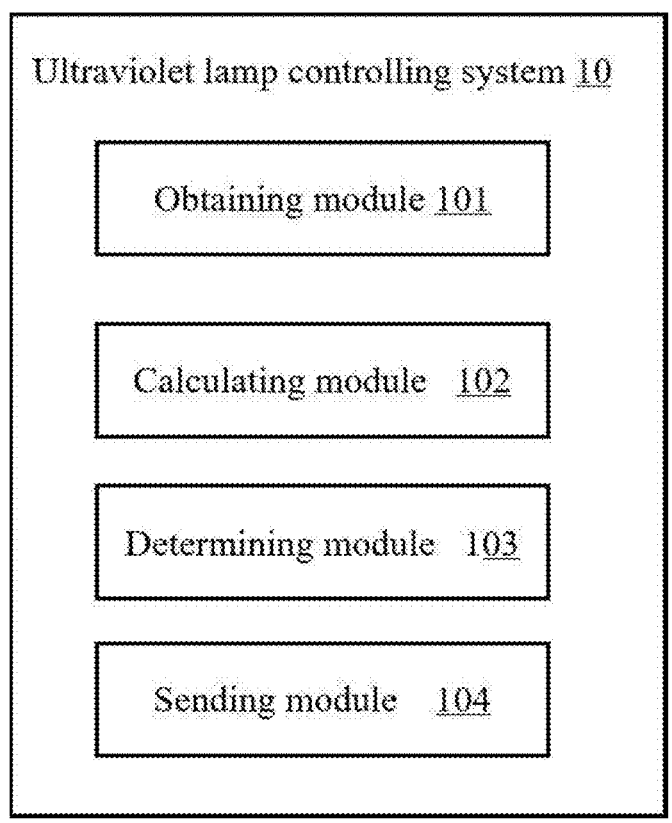
FIG. 4 is a block diagram of one embodiment of a system for controlling the ultraviolet lamp.

Referring to FIG. 4, in at least one embodiment, an ultraviolet lamp controlling system 10 can be divided into multiple modules based on the functions it performs. The one or more modules are stored in the storage device 11 and executed by at least one processor (the processor 12 in this embodiment) to complete the application. The one or more modules may be a series of computer program instruction segments capable of performing specific functions. The instruction segments are used to describe the execution process of the ultraviolet lamp controlling system 10 in the electronic device 1. For example, the ultraviolet lamp controlling system 10 may be divided into an obtaining module 101, a calculating module 102, a determining module 103, and a sending module 104.

In at least one embodiment, the obtaining module 101 can obtain tilt data of the platform of the machine 3, and the tilt data can include a tilt direction and a tilt angle.

In at least one embodiment, in an initial state, the platform of the machine 3 and the ultraviolet lamp 21 are at the same level, and a product to be irradiated is placed on the platform of the machine 3.

It should be noted that during a manufacturing process, the electronic device 1 can obtain the tilt data of the platform of the machine 3 in real time.

In at least one embodiment, the machine 3 can include a tilt sensor which is placed on the platform, and the tilt sensor can detect the tilt data of the platform of the machine 3. The tilt sensor can communicate with the electronic device 1. It should be noted that the tilt sensor may be a dual-axis tilt sensor, which can detect the tilt angle and the tilt direction of the platform of the machine 3, and send the tilt angle and the tilt direction to the electronic device 1.

In at least one embodiment, the calculating module 102 can calculate a tilt amplitude of the platform of the machine 3 based on the tilt data.

In at least one embodiment, the electronic device 1 can calculate the tilt amplitude of the platform of the machine 3 based on the tilt angle and the tilt direction. The electronic device 1 can establish a coordinate system based on the platform when the machine 3 is in an initial horizontal state, where an origin of the coordinate system is a point of a lower left corner of the platform, an X-axis of the coordinate system is a length of the platform, and a Y-axis of the coordinate system is a width of the platform. The electronic device 1 can calculate a first tilt amplitude of the platform of the machine 3 in the X-axis direction based on the length of the machine 3 in the X-axis direction and the tilt angle, and calculate a second tilt amplitude of the platform of the machine 3 in the Y-axis direction based on the width of the machine 3 in the Y-axis direction and the tilt angle.

In at least one embodiment, the tilt amplitude of the platform of the machine 3 can include a first tilt width of the platform of the machine 3 in the X-axis direction and a second tilt width of the platform of the machine 3 in the Y-axis direction of the coordinate system. When the platform of the machine 3 is tilted below the horizontal plane, the tilt amplitude is negative, and when the platform of the machine 3 is tilted above the horizontal plane, the tilt amplitude is positive.

In at least one embodiment, the determining module 103 can determine a target ultraviolet lamp to be adjusted based on the tilt direction.

In at least one embodiment, the electronic device 1 can determine a tilted portion of the platform of the machine 3 based on the tilt direction, and determine the target ultraviolet lamp based on the tilted portion of the platform of the machine 3. In at least one embodiment, the electronic device 1 can pre-store a correspondence table between the tilted portion of the platform of the machine 3 and the ultraviolet lamp 21. Then, the electronic device 1 can determine the target ultraviolet lamp based on the tilted portion of the platform of the machine 3 by querying the correspondence table.

For example, the platform of the machine 3 is rectangular in shape. There are at least four ultraviolet lamps 21. The four ultraviolet lamps 21 are set in line with four corners of the platform of the machine 3, so that the product can be evenly irradiated. For example, the four ultraviolet lamps 21 can include a first ultraviolet lamp, a second ultraviolet lamp, a third ultraviolet lamp, and a fourth ultraviolet lamp. The first ultraviolet lamp corresponds to an upper left corner of the platform of the machine 3, the second ultraviolet lamp corresponds to a lower left corner of the platform of the machine 3, the third ultraviolet lamp corresponds to an upper right corner of the platform of the machine 3, and the fourth ultraviolet lamp corresponds to a lower right corner of the platform of the machine 3.

In at least one embodiment, when the platform of the machine 3 is tilted, the electronic device 1 can determine the target ultraviolet lamp according to the tilt direction of the machine 3. For example, when the platform of the machine 3 is tilted to the lower left corner, the electronic device 1 can determine that the tilted portion of the platform of the machine 3 is the lower left corner through the tilt sensor, and determine that the second ultraviolet lamp is the target ultraviolet lamp. When the platform of the machine 3 is tilted to the upper left corner, the electronic device 1 can determine that the tilted portion of the platform of the machine 3 is the upper left corner through the tilt sensor, and determine that the first ultraviolet lamp is the target ultraviolet lamp. When the platform of the machine 3 is tilted to the lower right corner, the electronic device 1 can determine that the tilted portion of the platform of the machine 3 is the lower right corner through the tilt sensor, and determine that the fourth ultraviolet lamp is the target ultraviolet lamp. When the platform of the machine 3 is tilted to the upper right corner, the electronic device 1 can determine that the tilted portion of the platform of the machine 3 is the upper right corner through the tilt sensor, and determine that the third ultraviolet lamp is the target ultraviolet lamp.

In at least one embodiment, the obtaining module 101 can obtain an adjustment range of the target ultraviolet lamp based on the tilt amplitude.

In at least one embodiment, the electronic device 1 can obtain the adjustment range based on the tilt amplitude after determining the target ultraviolet lamp, and make the ultraviolet light emitted by the target ultraviolet lamp and the product to be irradiated are at the same level.

In at least one embodiment, the sending module 104 can send the adjustment range to the ultraviolet lamp adjustment device 2 to adjust the target ultraviolet lamp based on the adjustment range.

In at least one embodiment, the electronic device 1 can send the adjustment range to the ultraviolet lamp adjustment device 2. The controller 20 of the ultraviolet lamp adjustment device 2 controls the motor 22 to rotate the connecting device 24 connected to the target ultraviolet lamp to move the target ultraviolet lamp upward or downward, so that the ultraviolet light emitted by the target ultraviolet lamp can illuminate the product to be irradiated on the platform in parallel. That is, the ultraviolet light emitted by the target ultraviolet lamp and the product to be irradiated are on the same horizontal plane, as shown in FIG. 3.

The modules/units integrated by the electronic device 1 can be stored in a computer readable storage medium if implemented in the form of a software functional unit and sold or used as a stand-alone product. The present disclosure implements all or part of the processes in the foregoing embodiments, and a computer program may also instruct related hardware. The computer program may be stored in a computer readable storage medium. The steps of the various method embodiments described above may be implemented by a computer program when executed by a processor. Wherein, the computer program comprises computer program code, which may be in the form of source code, product code form, executable file, or some intermediate form. The computer readable medium may include any entity or device capable of carrying the computer program code, a recording medium, a USB flash drive, a removable hard disk, a magnetic disk, an optical disk, a computer memory, a read-only memory (ROM), random access memory (RAM), electrical carrier signals, telecommunications signals, and software distribution media. It should be noted that the content contained in the computer readable medium may be increased or decreased according to the requirements of legislation and patent practice in a jurisdiction, for example, in some jurisdictions, computer-readable media does not include electrical carrier signals and telecommunication signals.

It can be understood that the module division described above is a division according to logical function, there may be other manners of division in actual implementation. In addition, the functional modules in the embodiments of the present application may be integrated in the same processing unit, or each module may exist alone physically, or two or more modules may be integrated in the same unit. The above integrated modules can be implemented in the form of hardware, or in the form of hardware plus software function modules.

It should be emphasized that the above-described embodiments of the present disclosure, including any embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. An electronic device comprising:
   at least one processor, and
   a storage device storing one or more programs that, when executed by the at least one processor, cause the at least one processor to:
   obtain tilt data of a platform of a machine, the tilt data comprising a tilt direction and a tilt angle;
   calculate a tilt amplitude of the platform of the machine based on the tilt data;
   determine a target ultraviolet lamp to be adjusted based on the tilt direction;
   obtain an adjustment range of the target ultraviolet lamp based on the calculated tilt amplitude; and
   send the adjustment range to an ultraviolet lamp adjustment device to adjust the target ultraviolet lamp, ultraviolet light emitted by the target ultraviolet lamp illuminating a product to be irradiated on the platform in parallel.

2. The electronic device of claim 1, wherein the at least one processor is further caused to:
   obtain the tilt data from a tilt sensor of the machine, wherein the tilt sensor is set on the platform of the machine and communicated with the electronic device.

3. The electronic device of claim 1, wherein the at least one processor is further caused to:
   pre-store a correspondence table between a portion of the platform of the machine and the ultraviolet lamp;
   determine a tilted portion of the platform of the machine based on the tilt direction;
   determine the target ultraviolet lamp based on the tilted portion of the platform of the machine by querying the correspondence table.

4. The electronic device of claim 1, wherein the tilt amplitude of the platform of the machine comprises a first tilt amplitude of the platform of the machine in an X-axis direction, and a second tilt amplitude of the platform of the machine in a Y-axis direction.

5. The electronic device of claim 4, wherein the at least one processor is further caused to:
   establish a coordinate system based on the platform when the machine is in an initial horizontal state, wherein an origin of the coordinate system is a point of a lower left corner of the platform, an X-axis of the coordinate system is a length of the platform, and a Y-axis of the coordinate system is a width of the platform;
   calculate the first tilt amplitude of the platform based on the length of the platform in the X-axis direction and the tilt angle; and
   calculate the second tilt amplitude of the platform based on the width of the platform in the Y-axis direction and the tilt angle.

6. An ultraviolet lamp controlling method applicable in an electronic device, the method comprising:
  obtaining tilt data of a platform of a machine, the tilt data comprising a tilt direction and a tilt angle;
  calculating a tilt amplitude of the platform of the machine based on the tilt data;
  determining a target ultraviolet lamp to be adjusted based on the tilt direction;
  obtaining an adjustment range of the target ultraviolet lamp based on the calculated tilt amplitude; and
  sending the adjustment range to an ultraviolet lamp adjustment device to adjust the target ultraviolet lamp, ultraviolet light emitted by the target ultraviolet lamp illuminating a product to be irradiated on the platform in parallel.

7. The method of claim 6, wherein the method further comprises:
  obtaining the tilt data from a tilt sensor of the machine, wherein the tilt sensor is set on the platform of the machine and communicated with the electronic device.

8. The method of claim 6, wherein the method further comprises:
  pre-storing a correspondence table between a portion of the platform of the machine and the ultraviolet lamp;
  determining a tilted portion of the platform of the machine based on the tilt direction;
  determining the target ultraviolet lamp based on the tilted portion of the platform of the machine by querying the correspondence table.

9. The method of claim 6, wherein the tilt amplitude of the platform of the machine comprises a first tilt amplitude of the platform of the machine in an X-axis direction, and a second tilt amplitude of the platform of the machine in a Y-axis direction.

10. The method of claim 9, wherein the method further comprises:
  establishing a coordinate system based on the platform when the machine is in an initial horizontal state, wherein an origin of the coordinate system is a point of a lower left corner of the platform, an X-axis of the coordinate system is a length of the platform, and a Y-axis of the coordinate system is a width of the platform;
  calculating the first tilt amplitude of the platform based on the length of the platform in the X-axis direction and the tilt angle; and
  calculating the second tilt amplitude of the platform based on the width of the platform in the Y-axis direction and the tilt angle.

11. A non-transitory storage medium having stored thereon instructions that, when executed by at least one processor of an electronic device, causes the at least one processor to perform an ultraviolet lamp controlling method the method comprising:
  obtaining tilt data of a platform of a machine, the tilt data comprising a tilt direction and a tilt angle;
  calculating a tilt amplitude of the platform of the machine based on the tilt data;
  determining a target ultraviolet lamp to be adjusted based on the tilt direction;
  obtaining an adjustment range of the target ultraviolet lamp based on the calculated tilt amplitude; and
  sending the adjustment range to an ultraviolet lamp adjustment device to adjust the target ultraviolet lamp, ultraviolet light emitted by the target ultraviolet lamp illuminating a product to be irradiated on the platform in parallel.

12. The non-transitory storage medium of claim 11, wherein the method further comprises:
  obtaining the tilt data from a tilt sensor of the machine, wherein the tilt sensor is set on the platform of the machine and communicated with the electronic device.

13. The non-transitory storage medium of claim 11, wherein the method further comprises:
  pre-storing a correspondence table between a portion of the platform of the machine and the ultraviolet lamp;
  determining a tilted portion of the platform of the machine based on the tilt direction;
  determining the target ultraviolet lamp based on the tilted portion of the platform of the machine by querying the correspondence table.

14. The non-transitory storage medium of claim 11, wherein the tilt amplitude of the platform of the machine comprises a first tilt amplitude of the platform of the machine in an X-axis direction, and a second tilt amplitude of the platform of the machine in a Y-axis direction.

15. The non-transitory storage medium of claim 14, wherein the method further comprises:
  establishing a coordinate system based on the platform when the machine is in an initial horizontal state, wherein an origin of the coordinate system is a point of a lower left corner of the platform, an X-axis of the coordinate system is a length of the platform, and a Y-axis of the coordinate system is a width of the platform;
  calculating the first tilt amplitude of the platform based on the length of the platform in the X-axis direction and the tilt angle; and
  calculating the second tilt amplitude of the platform based on the width of the platform in the Y-axis direction and the tilt angle.

* * * * *